United States Patent
Kanazawa et al.

(10) Patent No.: US 9,848,768 B2
(45) Date of Patent: Dec. 26, 2017

(54) TARGET PRESENTING APPARATUS

(71) Applicant: NIDEK CO., LTD., Aichi (JP)

(72) Inventors: Yuichiro Kanazawa, Aichi (JP); Noriji Kawai, Aichi (JP); Ryoji Suzuki, Aichi (JP); Toshihiro Kobayashi, Aichi (JP); Yukito Hirayama, Aichi (JP); Kazunori Shibata, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/724,990

(22) Filed: May 29, 2015

(65) Prior Publication Data

US 2015/0342455 A1    Dec. 3, 2015

(30) Foreign Application Priority Data

Jun. 2, 2014   (JP) .................................. 2014-114187
May 13, 2015  (JP) .................................. 2015-098235

(51) Int. Cl.
| | | |
|---|---|---|
| A61B 3/02 | (2006.01) | |
| A61B 3/14 | (2006.01) | |
| A61B 3/10 | (2006.01) | |
| G02B 27/14 | (2006.01) | |
| A61B 3/032 | (2006.01) | |

(52) U.S. Cl.
CPC .................................. *A61B 3/032* (2013.01)

(58) Field of Classification Search
CPC ............ G02B 27/0172; G02B 27/0101; G02B 2027/0178; G02B 2027/0132; G02B 2027/011; G02B 27/01; A61B 3/032; A61B 3/103; A61B 3/1015; A61B 3/14; A61B 3/113; A61B 3/1208; A61B 3/1225; A61B 3/024

USPC ................ 351/243, 200, 239, 246, 205–206, 351/210–211, 218, 220–223; 359/443, 359/13–14, 603–636; 345/7, 9, 156; 348/115; 353/119; 349/11

See application file for complete search history.

(56) References Cited

U.S. PATENT DOCUMENTS

| | | | | |
|---|---|---|---|---|
| 5,671,087 A | * | 9/1997 | Kawamura | ........ G02B 27/0172 348/E13.041 |
| 5,754,344 A | * | 5/1998 | Fujiyama | ........... G02B 27/0172 348/E13.014 |
| 6,422,700 B2 | * | 7/2002 | Ohyagi | .......................... 351/239 |
| 2002/0047987 A1 | * | 4/2002 | Massengill | ............ A61B 3/024 351/204 |
| 2005/0040940 A1 | * | 2/2005 | Sonobe | .................. B60K 37/02 340/438 |
| 2012/0120499 A1 | * | 5/2012 | Harrison | ................ G02B 17/06 359/631 |
| 2012/0243102 A1 | * | 9/2012 | Takeda | .................. G02B 17/086 359/630 |

(Continued)

FOREIGN PATENT DOCUMENTS

JP   2010-082253   4/2010

*Primary Examiner* — Dawayne A Pinkney
(74) *Attorney, Agent, or Firm* — Rankin, Hill & Clark LLP

(57) ABSTRACT

A target presenting apparatus includes: a display for emitting a target light flux; a concave mirror for receiving the target light flux in such a manner as to displace the target light flux from an optical axis thereof; a housing for accommodating the concave mirror and the display therein; and an optical member, placed in the housing, for guiding the target light flux from the inside to the outside of the housing to present a target to an examinee.

15 Claims, 7 Drawing Sheets

(56) References Cited

U.S. PATENT DOCUMENTS

| | | | |
|---|---|---|---|
| 2014/0177063 A1* | 6/2014 | Wang | G02B 5/30 |
| | | | 359/630 |
| 2014/0185012 A1* | 7/2014 | Kanazawa | A61B 3/18 |
| | | | 351/237 |
| 2014/0266986 A1* | 9/2014 | Magyari | G02B 27/0172 |
| | | | 345/8 |

* cited by examiner

TARGET PRESENTING APPARATUS

CROSS-REFERENCE TO RELATED APPLICATION

This application claims priority from Japanese Patent Application Nos. 2014-114187 filed on Jun. 2, 2014, and 2015-098235 filed on May 13, 2015, with the Japan Patent Office the entire contents of which are hereby incorporated by reference.

BACKGROUND

1. Technical Field

An embodiment of the present disclosure relates to a target presenting apparatus that presents an examination target for a visual function test.

2. Description of the Related Art

A known target presenting apparatus that presents an examinee with an optometry target presents, for example, a target light flux formed by illuminating a chart plate, as the optometry target, through a presentation window via a concave mirror and a beam splitter (see JP-A-2010-082253). In such an apparatus, for example, the target light flux that has passed through the chart plate passes through the beam splitter and is reflected by the concave mirror, and then is reflected by the beam splitter and guided to an examinee's eye.

SUMMARY

A target presenting apparatus according to one embodiment of the present disclosure includes: a display for emitting a target light flux; a concave mirror for receiving the target light flux in such a manner as to displace the target light flux from an optical axis thereof; a housing for accommodating the concave mirror and the display therein; and an optical member, placed in the housing, for guiding the target light flux from the inside to the outside of the housing to present a target to an examinee.

DESCRIPTION OF THE EMBODIMENTS

Figure 1:
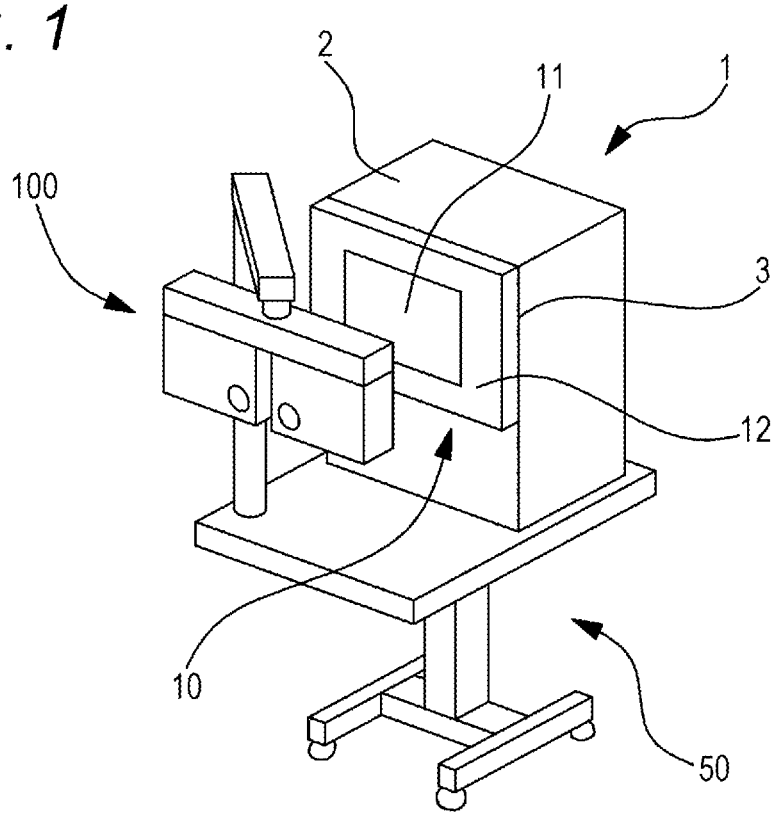
FIG. 1 illustrates an exterior view of a target presenting apparatus (the apparatus) according to one example of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

A general apparatus may use a display instead of the chart plate. In this case, the accuracy of the examination may be reduced due to, for example, a reduction in the amount of light of a target light flux presented to an examinee.

One object of the present disclosure is to provide a space-saving target presenting apparatus that can promote space saving and present a target for an excellent examination, and uses a display to display the target.

One embodiment of the present disclosure will be described hereinafter with reference to the drawings. FIGS. 1 to 8 are diagrams illustrating the configuration of a target presenting apparatus according to the embodiment.

A target presenting apparatus 1 (may be abbreviated hereinafter to the apparatus 1) of the embodiment is an apparatus for presenting an examinee with an examination target for a visual acuity examination. The target presenting apparatus 1 mainly includes a concave mirror 22, a display 21, a housing 2, and an optical member 23 (see FIGS. 1 and 2).

The concave mirror 22 reflects a target light flux from the display 21. A distance between the display 21 and an examinees eye E is set to, for example, a distance-examination distance. The distance-examination distance is a distance used for examining the distance visual acuity of the examinee's eye E. The distance-examination distance is, for example, approximately 5 to 7 m.

The display 21 presents the examinee's eye E with the target light flux. The display 21 displays, for example, a distance-examination target and a near-examination target. The display 21 may be, for example, an LCD (Liquid Crystal Display) or organic EL (Electro Luminescence). The display 21 includes a screen for emitting (projecting) the target light flux. The display 21 may be placed in such a manner as that the direction of the normal to the screen of the display 21 is inclined with respect to an optical axis O1 of the concave mirror 22. For example, the display 21 may emit the target light flux in such a manner as that an optical axis L1 of the target light flux is inclined with respect to the optical axis O1 of the concave mirror 22. For example, the display 21 may emit the target light flux to the concave mirror 22 in such a manner as to displace the target light flux from the optical axis O1 of the concave mirror 22. For example, the display 21 may emit the target light flux from an oblique direction with respect to the optical axis O1 toward an intersection point of a reflection surface of the concave mirror 22 and the optical axis O1. In other words, in the apparatus 1, the concave mirror 22 may be configured to receive the target light flux in such a manner as to displace the target light flux from its own optical axis O1.

The housing 2 is, for example, a box with an opening. The housing 2 may accommodate therein, for example, the concave mirror 22, the display 21, and the optical member 23. The housing 2 may be configured, for example, to be mounted on a table or the like.

The optical member 23 reflects, for example, the target light flux emitted from the display 21 and reflected by the concave mirror 22. The optical member 23 guides, for example, the target light flux from the inside to the outside of the housing 2 and presents the examinee with the target. The optical member 23 has, for example, a function of changing the light travel direction. The optical member 23 may be, for example, a total reflection mirror, half mirror, beam splitter, or prism. The optical member 23 may be placed, for example, outside an optical path of a first optical path (for example, an optical path having the optical axis L1 as an optical axis) set to emit (project) the target light flux from the display 21 to the concave mirror 22. In other words, the optical member 23 may be placed at a position deviating from the first optical path being the optical path of the target light flux travelling from the display 21 to the concave mirror 22. Consequently, it is allowed to reduce a possibility that the target light flux of the display 21 is blocked by the optical member 23.

For example, the display 21 may be placed in an upper part of the housing 2. In this case, the display 21 may emit (project) the target light flux downward. For example, the screen of the display 21 may be pointed downward in the housing 2.

Furthermore, for example, the concave mirror 22 may be placed in a lower part of the housing 2. In this case, the concave mirror 22 may reflect the target light flux from the display 21, for example, upward in the housing 2. For example, the optical member 23 may be configured to guide, toward the examinee, the target light flux reflected by the concave mirror 22 and travelling upward. In this manner, the display 21 and the concave mirror 22 may be placed in the up-down direction, for example, to reduce the installation space of the apparatus 1.

The display 21 of the embodiment may be placed closer to the examinee than the optical member 23. If the display 21 is placed on the examinee side of the optical member 23, an inclination angle θ of the optical member 23 with respect to the up-down direction is increased (see FIG. 4). Hence, the area of the target light flux, which is shielded by the optical member 23, is increased. In this case, the display 21 is placed, for example, at a position far from the optical member 23 to avoid the shielding of the target light flux by the optical member 23. Therefore, the size of the apparatus 1 is increased. Furthermore, an angle α of incidence to the concave mirror 22 is increased so that the distortion of the target is increased. As described above, for example, the installation space of the apparatus may be reduced while the possibility is reduced that the target light flux emitted from the display 21 is blocked by the optical member 23.

Figure 2:
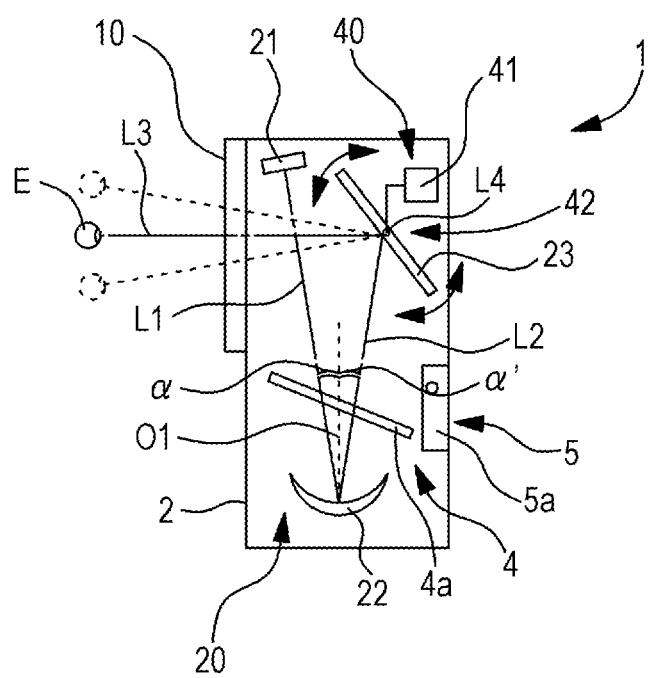
FIG. 2 is a schematic diagram illustrating an optical system of the apparatus.

The apparatus 1 may include a driving unit 40 (see FIG. 2). The driving unit 40 may hold, for example, the optical member 23 in a drivable manner. For example, the driving unit 40 may drive the optical member 23 (for example, change the attitude of the optical member 23) to change (adjust) an optical path for guiding, to the examinee, the target light flux reflected by the concave mirror 22. Consequently, the optical path of the target light flux may be adjusted to agree with the height of the eye line of the examinee.

The apparatus 1 may include, for example, a prevention unit (preventer) 4. The prevention unit 4 may prevent, for example, the concave mirror 22 from becoming dirty. For example, the prevention unit 4 may include a shielding member 4a. It is preferable that the shielding member 4a transmit, for example, at least the target light flux emitted from the display 21. Consequently, it is allowed to reduce the possibility that dirt on the concave mirror 22 causes a problem in the target presented to the examinee. The prevention unit 4 may drive the shielding member 4a (move the shielding member 4a) when the display 21 presents the target to the examinee's eye E to withdraw the shielding member 4a to a position that does not shield the target light flux.

The apparatus 1 may include, for example, a near-far switching part 30 (see FIGS. 5 to 8). The near-far switching part 30 can switch a target presentation position (for example, the position of the display 21), for example, in accordance with which of the distance examination and the near examination is performed. Consequently, for example, the common display 21 is used to enable the presentation of the target to the examinee from both a presentation position for far use and a presentation position for near use. The near-far switching part 30 may include, for example, a far-use holder 31 and a near-use holder 32. The far-use holder 31 may hold, for example, the display 21 detachably at a presentation position for a distance visual acuity examination (the presentation position for far use) for the examinee (examinee's eye E). The near-use holder 32 may hold, for example, the display 21 detachably at a presentation position for a near visual acuity examination (the presentation position for near use) for the examinee (examinee's eye E).

Figure 6:
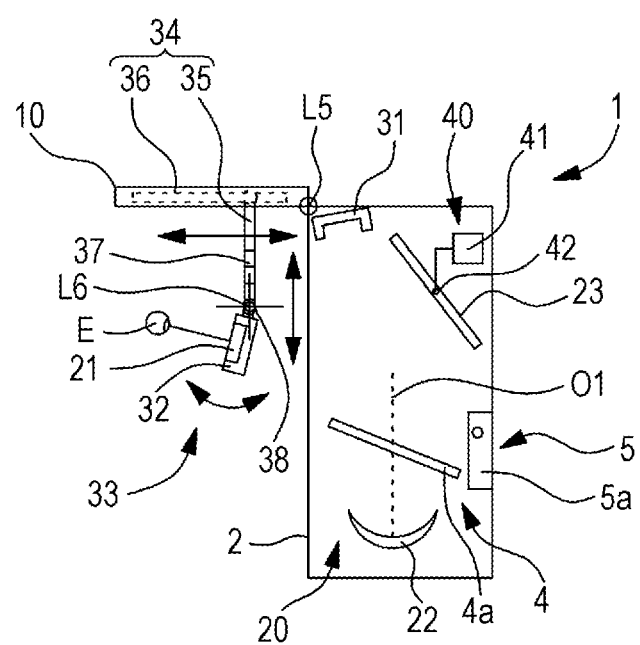
FIG. 6 is a schematic diagram illustrating an example of the near-far switching part.

The apparatus 1 may include a back-and-forth movement unit (back-and-forth movement part) 34 (see FIG. 6). The back-and-forth movement unit 34 may move, for example, the near-use holder 32 in a front-back direction with respect to the examinee. Consequently, the back-and-forth movement unit 34 may change the distance to present a near target upon the near examination.

The apparatus 1 may include an up-and-down movement unit (up-and-down movement part) 37. The up-and-down movement unit 37 may move, for example, the near-use holder 32 in an up-down direction with respect to the examinee. Consequently, the up-and-down movement unit 37 may change the height to present the near target upon the near examination.

The apparatus 1 may include an angle adjustment unit (angle adjuster) 38. The angle adjustment unit 38 may turn, for example, the near-use holder 32 toward the examinee side. The angle adjustment unit 38 may turn the near-use holder 32 toward the examinee side to change the angle of the screen of the display 21 held by the near-use holder 32. The angle adjustment unit 38 may rotate, for example, the near-use holder 32 about a horizontal axis with respect to the examinee.

EXAMPLE

The target presenting apparatus (the apparatus) 1 of the example will be described hereinafter. The apparatus 1 is an apparatus for presenting an examinee with an examination target for a visual acuity examination. The apparatus 1 may be set, for example, on an optometry table 50 upon use, as illustrated in FIG. 1. Upon use, the apparatus 1 may be placed, for example, in a position away from an optometry unit 100. The optometry unit 100 is, for example, a unit that includes unillustrated rotating discs with optical devices, switches among the optical devices and places the switched optical device in front of the examinee's eye E.

The apparatus 1 mainly includes a target presenting optical system 20 and the housing 2. The target presenting optical system 20 guides the target light flux to the examinee's eye E. The housing 2 accommodates the target presenting optical system 20 therein.

<Housing>

The housing 2 of the example accommodates therein the display 21, the concave mirror 22, and the optical member 23 as illustrated in FIG. 2. The housing 2 of the example has a shape that extends in the up-down direction of the examinee. As illustrated in FIG. 1, a presentation window 3 is provided on the examinee side of the housing 2. The presentation window 3 is configured to prevent the entry of dust and the like into the housing 2 by, for example, being blocked by a protection panel 10. The protection panel 10 mainly includes a transparent panel 11 and a shielding part 12. The material of the transparent panel 11 is, for example, a transparent member such as an acrylic resin or glass plate. The shielding part 12 is placed around the transparent panel 11. The transparent panel 11 transmits the target light flux emitted from the target presenting optical system 20 in the housing 2. Consequently, the target light flux is emitted to the outside of the housing 2. The examinee can observe the examination target that has passed through the transparent panel 11.

<Control Part>

Figure 3:
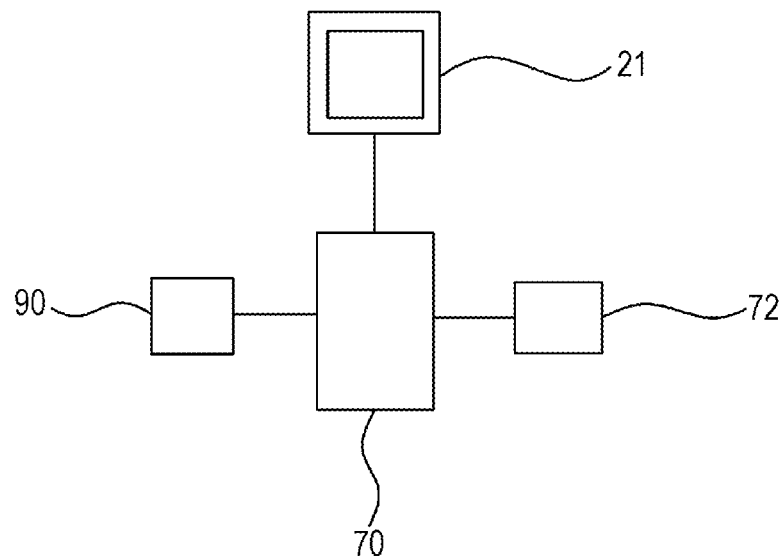
FIG. 3 is a block diagram illustrating a control system of the apparatus.

FIG. 3 is a control block diagram of the apparatus 1. As illustrated in FIG. 3, the apparatus 1 includes a control part 70, a controller 90, and a memory 72. The control part 70 is connected to the display 21, the controller 90, the memory 72, and the like. The control part 70 and the memory 72 are accommodated in, for example, the housing 2. The controller 90 is attached to, for example, an outer wall of the housing 2. Data on many examination targets such as Landolt rings is stored in the memory 72. For example, target data of visual acuity values of 0.1 to 2.0 is stored in the memory 72. The control part 70 calls appropriate target data from the memory 72 in response to an input signal from the controller 90. Furthermore, the control part 70 displays a target on the screen of the display 21 by controlling the display 21. In the example, the signal from the controller 90 may be input into the control part 70 via an unillustrated cable, or may be input into the control part 70 by wireless communication such as infrared.

<Target Presenting Optical System>

In the target presenting optical system 20 illustrated in FIG. 2, the target light flux from the display 21 placed in the housing 2 is reflected by the concave mirror 22 and the optical member 23 and travels to the examinee's eye E. Consequently, the target is optically presented to the examinee's eye E at a predetermined distance-examination distance (for example, an examination distance of 5 m). The target presenting optical system 20 includes, for example, the display 21, the concave mirror 22, and the optical member 23.

The display 21 displays targets such as distance-examination targets and near-examination targets. For example, examination targets such as Landolt rings are displayed on the display 21. For example, an LCD (Liquid Crystal Display) or organic EL (Electro Luminescence) is used as the display 21. In the example, a case where an LCD is used as the display 21 is described as an example. The concave mirror 22 sets the target presentation distance to the distance-examination distance. For example, in terms of the focal length of the concave mirror 22, it is designed in such a manner as that the optical distance between the display 21 and the examinee's eye E is an examination distance of 5 m. The optical member 23 guides the examination target to the examinee's eye E. The optical member 23 includes, for example, a total reflection mirror, half mirror, or prism.

The placement of each member in the target presenting optical system 20 is described with reference to FIG. 2. The display 21 is placed in the upper part and on the examinee side in the housing 2. The display 21 is placed in such a manner as to point the screen downward and emits the target light flux downward. For example, the display 21 emits the target light flux in the direction of the optical axis L1 as illustrated in FIG. 2. The display 21 may emit the target light flux directly downward or obliquely downward.

The concave mirror 22 is placed in a bottom portion in the housing 2. The concave mirror 22 is placed in such a manner as to point its reflection surface upward. The concave mirror 22 reflects upward the target light flux emitted from the display 21. For example, the concave mirror 22 reflects the target light flux in the direction of an optical axis L2 as illustrated in FIG. 2. The concave mirror 22 may reflect the target light flux directly upward or obliquely upward.

The concave mirror 22 reflects, toward the optical member 23, the target light flux from the display 21. Hence, the concave mirror 22 is placed in such a manner as that the optical axis O1 of the concave mirror 22 is inclined with respect to the optical axis L1 of the display 21 (the direction of the normal to the screen).

The optical member 23 is placed in the upper part and in the further back than the display 21 as viewed from the examinee, in the housing 2. The optical member 23 reflects, toward the examinee's eye E, the target light flux reflected from the concave mirror 22. For example, the optical member 23 is placed on the optical axis L2 of the concave mirror 22, which is a reflection axis of the optical axis L1. For example, the optical member 23 reflects the target light flux in the direction of an optical axis L3 for presenting a target to the examinee's eye E, as illustrated in FIG. 2.

As described above, the optical axis L1 is set to project (emit) a target (target light flux) from the display 21 to the concave mirror 22. The optical axis L3 is set to project the target from the front direction to the examinee's eye E. The positional relationship between these optical axes L1 and L3 is a perpendicular positional relationship. The perpendicular positional relationship includes not only a positional relationship where the angle formed by the optical axes L1 and L3 is 90° but also a positional relationship where the angle formed by the optical axes L1 and L3 is an angle deviating slightly from 90 degrees (for example, an angle deviating by approximately 5° from 90°).

The optical member 23 is preferable to be placed at a position deviating from the optical axis L1 of the target light flux emitted from the display 21. Consequently, it is allowed to avoid the optical member 23 blocking the target light flux from the display 21.

Figure 4:
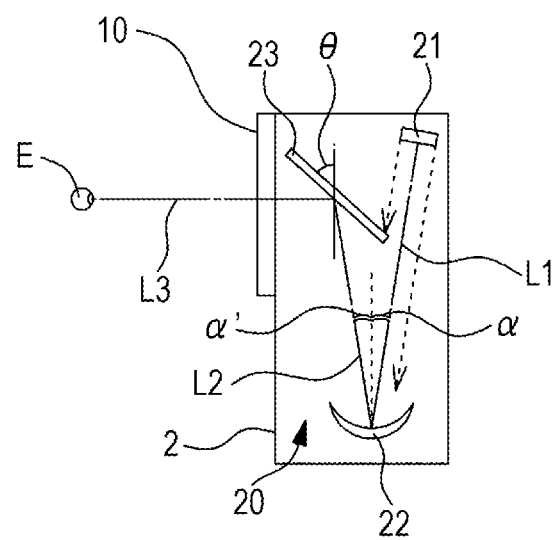
FIG. 4 is a diagram illustrating an example of the optical system of the apparatus.

The placement of the display 21 closer to the examinee than the optical member 23 reduces the area restricted by the optical member 23 in the visual field of the examinee. Suppose the optical member 23 is placed closer to the examinee than the display 21 as illustrated in FIG. 4. In this case, the inclination angle θ of the optical member 23 with respect to the up-down direction is increased as compared to the case where the display 21 is placed closer to the examinee than the optical member 23. Consequently, the area of the target light flux restricted (shielded) by the optical member 23 is increased. Therefore, in order to prevent or suppress the target light flux emitted from the display 21 from being blocked by the optical member 23, the display 21 is located away from the optical member 23 and accordingly the incidence angle α (or reflection angle α') of the target light flux to the concave mirror 22 is increased. If the incidence angle α of the target light flux to the concave mirror 22 is increased, there occur problems such as that the distortion of the target is increased and a space for the target presenting optical system 20 is increased. From the above points, the display 21 is preferable to be placed closer to the examinee than the optical member 23.

The display 21 is placed closer to the examinee than the optical member 23 and accordingly the incidence angle α (and the reflection angle α') can be reduced. The incidence angle α is an angle of incidence to the concave mirror 22 of the target light flux emitted from the display 21. The reflection angle α' is an angle of reflection from the concave mirror 22 of the target light flux. Consequently, the distortion of the examination target by the concave mirror 22 may be reduced or the front-back width of the entire apparatus may be reduced.

The apparatus 1 may include the driving unit 40 for driving the optical member 23. The driving unit 40 may drive the optical member 23, for example, in a range that does not shield the target light flux of the display 21. For example, the control part 70 may change the direction of the optical axis L3 for presenting a target to the examinee's eye E by driving the optical member 23 with the driving unit 40. Consequently, even if the height of the examinee's eye E is different depending on the examinee, the target light flux can be accurately guided to the examinee's eye E by changing the direction of the optical axis L3. The driving unit 40 may drive the optical member 23 back and forth and/or up and down with respect to the examinee, or rotate the optical member 23 about the horizontal axis.

The configuration where the optical member 23 is rotated about the horizontal axis is described as an example of the driving unit 40. In this case, for example, the driving unit 40 may include a driving part 41 and a rotating shaft 42. The driving part 41 rotates the rotating shaft 42 about a horizontal axis L4. The rotating shaft 42 is coupled to the optical member 23. The rotating shaft 42 is rotated by the driving part 41 to rotate the optical member 23 about the horizontal axis LA. The control part 70 may control the rotation of the driving part 41 to adjust the angle of the optical member 23 in accordance with the height of the examinee's eye E. The control part 70 may adjust the angle of the optical member 23 with the driving unit 40 to make an adjustment in such a manner as that the optical axis L3 points toward the examinee's eye E. The height of the examinee's eye E may be input from the controller 90 based on an operation by an examiner. Alternatively, the control part 70 may detect the height of an optometric window of the optometry unit 100 as the height of the examinee's eye E.

<Near-Far Switching Part>

As illustrated in FIGS. 5 to 8, the apparatus 1 may include the near-far switching part 30. The near-far switching part 30 can switch the presentation position of a target displayed by the display 21 (the position of the display 21) in accordance with which of the distance examination and the near examination is performed. The near-far switching part 30 may include, for example, the far-use holder 31 and the near-use holder 32. The far-use holder 31 holds the display 21 detachably, for example, at a target presentation position for the distance examination with the target presenting optical system 20. The near-use holder 32 holds the display 21 detachably at a target presentation position for the near examination with the target presenting optical system 20. The near-far switching part 30 switches the setting of a member that holds the display 21 between the far-use holder 31 and the near-use holder 32 and accordingly can switch the target presentation position in accordance with which of the distance examination and the near examination is performed.

Figure 5:
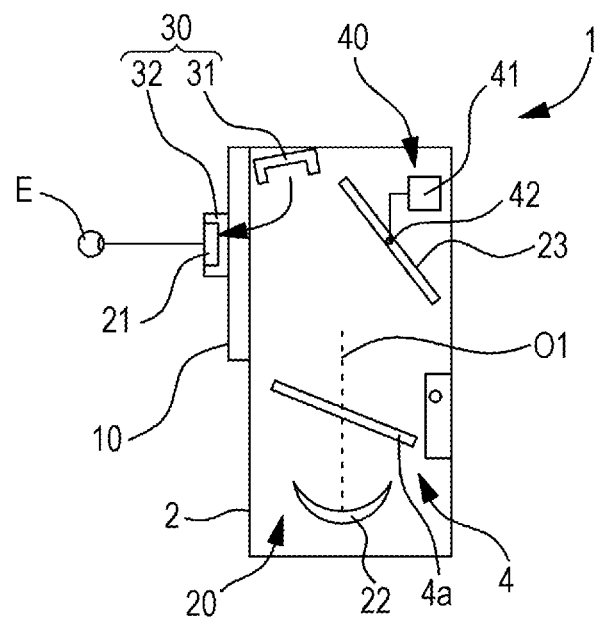
FIG. 5 is a schematic diagram illustrating an example of a near-far switching part.

The far-use holder 31 holds the display 21 detachably, for example, in the housing 2. The far-use holder 31 may have, for example, a shape into which the display 21 fits as illustrated in FIG. 5. The examiner can attach/detach the display 21 to/from the far-use holder 31 by sliding the display 21 in the left-right direction.

The near-use holder 32 holds the display 21 detachably, for example, outside the housing 2. The near-use holder 32 may, for example, be fixed to the protection panel 10 as illustrated in FIG. 5. The near-use holder 32 may have, for example, a shape into which the display 21 fits. The examiner can attach/detach the display 21 to/from the near-use holder 32 by sliding the display 21 in the left-right direction. The far-use holder 31 and the near-use holder 32 do not need to be of the slide type and may be of a type that sandwiches the display 21 with the elastic force of an elastic body such as a spring.

The apparatus 1 may further include a near-use adjuster 33 as illustrated in FIG. 6. The near-use adjuster 33 is provided to adjust the position of the display 21 upon the near examination. For example, the near-use adjuster 33 may include the back-and-forth movement part 34.

The back-and-forth movement part 34 may be configured to move the position of the display 21 in the front-back direction of the examinee. For example, the back-and-forth movement part 34 may move the near-use holder 32 in the front-back direction of the examinee to move the position of the display 21 held by the near-use holder 32. The position of the display 21 is moved in the front-back direction of the examinee and accordingly the target presentation distance for the near examination can be changed. For example, in terms of a distance from the display 21 to the examinee's eye E in the front-back direction, the back-and-forth movement part 34 may be able to move within a short distance of approximately 10 to 70 cm. Furthermore, the back-and-forth movement part 34 may be able to change the distance from the display 21 to the examinee's eye E in the front-back direction from short distance to middle distance (for example, approximately 1 m).

Figure 7:
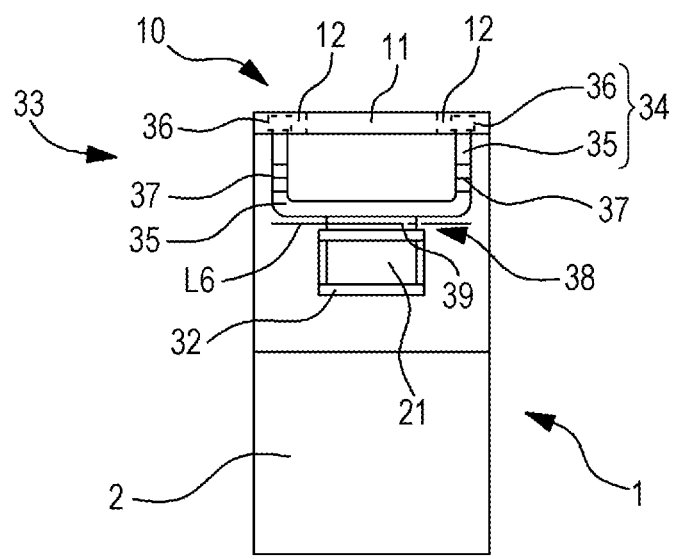
FIG. 7 is a schematic diagram illustrating the apparatus as viewed from an examinee side upon a near examination.

The back-and-forth movement part 34 includes, for example, a slide arm 35 and a guide groove 36 as illustrated in FIGS. 6 and 7. For example, the slide arm 35 moves the near-use holder 32 in the front-back direction of the examinee along the guide groove 36.

For example, the guide groove 36 may be provided on a back surface of the protection panel 10. For example, the guide grooves 36 may be provided on the left and right on the back surface of the protection panel 10.

For example, the slide arm 35 may have a U shape. In this case, one end of the slide arm 35, which divides into two parts, is coupled to the left and right guide grooves 36. The other end of the slide arm 35 is coupled to the near-use holder 32.

Upon the near examination, for example, the examiner opens the protection panel 10 frontward with a rotation axis L5 provided to the top of the protection panel 10 as the center of rotation. The rotation axis L5 at the top of the protection panel 10 may, for example, be provided with an unillustrated angle maintenance mechanism. The angle maintenance mechanism may maintain the protection panel 10 in a state of being open at a desired angle. For example, a ratchet mechanism may be used as the angle maintenance mechanism.

For example, the examiner stands the protection panel 10 horizontally to remove the display 21 from the far-use holder 31 in the housing 2. The display 21 is attached into the near-use holder 32 coupled to the slide arm 35. Next, the examiner may move the slide arm 35 in the front-back direction along the guide grooves 36 to change the position of the display 21.

Furthermore, the near-use adjuster 33 may include, for example, the up-and-down movement part 37. The up-and-down movement part 37 may move, for example, the position of the display 21 in the up-down direction of the examinee. For example, the up-and-down movement part 37 may move the near-use holder 32 in the up-down direction of the examinee to move the position of the display 21 held by the near-use holder 32. The position of the display 21 is moved in the up-down direction of the examinee and accordingly the height to present a target upon the near examination can be changed. Consequently, the target can be presented at a height corresponding to the visual line of the examinee.

The up-and-down movement part 37 may, for example, be provided to the slide arm 35 as illustrated in FIGS. 6 and 7. For example, the up-and-down movement part 37 extends/contracts the slide arm 35 in the up-down direction of the examinee. The up-and-down movement part 37 may, for example, be provided with an extendable mechanism such as a telescopic, link. When the slide arm 35 is extended/contracted in the up-down direction, the position of the near-use holder 32 coupled to the slide arm 35 moves in the up-down direction. In this manner, the up-and-down movement part 37 may move the near-use holder 32 in the up-down direction to move, in the up-down direction of the examinee, the position of the display 21 held by the near-use holder 32.

Furthermore, the near-use adjuster 33 may include, for example, the angle adjuster 38. The angle adjuster 38 changes, for example, the angle of the display 21 in the up-down direction of the examinee. For example, the angle adjuster 38 changes the angle of the near-use holder 32 in the up-down direction of the examinee. Consequently, the angle adjuster 38 may change the angle of the screen of the display 21 held by the near-use holder 32. The angle adjuster 38 changes the angle of the display 21 and accordingly can adjust the direction of the visual line of the examinee of when the examinee observes the display 21. Therefore, the near examination can be performed, for example, in a state where the examinee is looking down.

The angle adjuster 38 may be provided, for example, between the slide arm 35 and the near-use holder 32 as illustrated in FIGS. 6 and 7. The angle adjuster 38 may couple the near-use holder 32 rotatably to the slide arm 35. The angle adjuster 38 may include, for example, a rotating shaft 39 that extends in the horizontal direction. The angle adjuster 38 may rotate the rotating shaft 39 to rotate the near-use holder 32 about a horizontal axis L6 and accordingly change the angle of the near-use holder 32 in the up-down direction.

Figure 8:
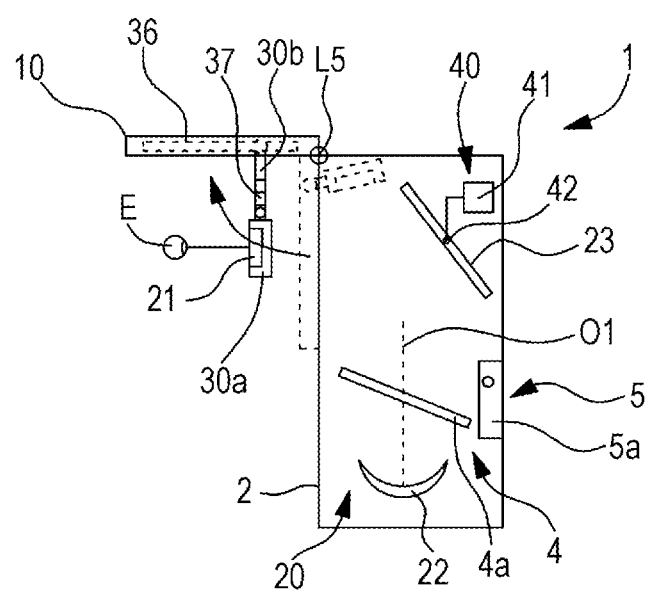
FIG. 8 is a schematic diagram illustrating an example of the near-far switching part.

The near-far switching part 30 may be configured to be used as both the far-use holder 31 and the near-use holder 32. For example, as illustrated in FIG. 8, a holder 30a used for both the distance examination and the near examination may be configured to be able to switch with a far-near switching arm 30b from the presentation position for far use to the presentation position for near use. Consequently, the position of the display 21 may be switched between the presentation position upon the distance examination and the presentation position upon the near examination.

<Examination Procedure>

A brief description is given of a visual function test using the target presenting apparatus 1 described above. The examiner instructs the examinee to look into the optometric window of the optometry unit 100.

When the distance examination is performed, a target light flux is emitted toward the concave mirror 22 from the display 21 held by the far-use holder 31. The target light flux reflected by the concave mirror 22 is then further reflected by the optical member 23 and presented to the examinee's eye E. The examinee observes the target through the optometry unit 100 and undergoes a distance visual function test. The control part 70 controls the display 21 based on a distance target selection signal input by the controller 90 to display a distance target on the display 21.

When the near examination is performed, the examiner, for example, opens the protection panel 10 frontward. The examiner then removes the display 21 from the far-use holder 31 in the housing 2. The examiner attaches the removed display 21 to the near-use holder 32. Consequently, the display 21 is held by the near-use holder 32 to be placed at a position away by a short distance (for example, 40 cm) from the examinee's eye E. The control part 70 controls the display 21 based on a near target selection signal input by the controller 90 to display a near target on the display 21. The examiner may move the near-use holder 32 with the back-and-forth movement part 34, the up-and-down movement part 37, and the angle adjuster 38 to adjust the position of the display 21.

As described above, in the apparatus 1, the display 21 and the concave mirror 22 may be placed along the up-down direction to reduce the thickness of the lateral width of the apparatus 1. Consequently, the space-saving target presenting apparatus may be provided.

In the apparatus 1, the display 21 and the concave mirror 22 are accommodated in the housing 2. In this manner, the target presenting optical system 20 (and the housing 2) may be configured to be independent of the optometry table 50, the optometry unit 100, and/or the like by integrating the target presenting optical system 20 in the housing 2. Therefore, the apparatus 1 may be a freestanding target presenting apparatus that can be installed on a general optometry table or the like.

As described above, the display 21 is placed closer to the examinee than the optical member 23 to facilitate the attachment/detachment of the display 21 to/from the examinee side of the apparatus 1. Therefore, it becomes easy to pull the display 21 frontward and place it in front of the examinee upon the near examination.

The apparatus 1 may include the prevention unit 4. The prevention unit 4 may prevent, for example, the concave mirror 22 from becoming dirty with dust and the like. The prevention unit 4 may include, for example, the shielding member 4a. The shielding member 4a of the example is placed above the concave mirror 22. The shielding member 4a is placed above the concave mirror 22 to reduce the possibility that dust and the like are attached to the concave mirror 22 and the concave mirror 22 becomes dirty. The prevention unit 4 may drive the shielding member 4a with, for example, an unillustrated driving part. Consequently, when a target is presented by the display 21, the prevention unit 4 may cause the driving part to withdraw the shielding member 4a.

The apparatus 1 may include a cleaning window 5. The cleaning window 5 is provided to the housing 2 to clean, for example, dust and the like attached to the shielding member 4a. For example, the cleaning window 5 may be provided with a door 5a. The examiner can open or block the cleaning window 5 by opening/closing the door 5a. The examiner can clean the shielding member 4a in the housing 2 easily through the cleaning window 5 by opening the door 5a of the cleaning window 5. The examiner can reduce the possibility that dust and the like enter the housing 2 by closing the door 5a of the cleaning window 5 after the end of the cleaning.

In the above description, it has been described that the apparatus 1 has the shape that extends in the up-down direction of the examinee. However, the shape of the apparatus 1 is not limited to this. For example, the apparatus 1 may have a shape that extends in the left-right direction of the examinee. In this case, the housing 2 may have a shape that extends in the left-right direction of the examinee. The display 21 and the concave mirror 22 may be placed in the left-right direction of the examinee. For example, the display 21 may be configured in such a manner as that the optical axis L1 of the target light flux emitted toward the concave mirror 22 extends in the left-right direction of the examinee. Also with such a configuration, the width in the front-back direction of the apparatus 1 can be reduced.

In the above configuration, it is preferable to adjust the incidence angle α and reflection angle α' of the target light flux in accordance with the curved surface shape (magnification) of the concave mirror 22. The incidence angle α is an angle of incidence to the concave mirror 22 of the target light flux emitted from the display 21. The reflection angle α' is an angle of reflection from the concave mirror 22 of the target light flux. The magnification of the concave mirror 22 is changed to also change the incidence and reflection angles that invite distortion. For example, when the concave mirror 22 with a higher magnification than that of the concave mirror 22 of the example is used, the incidence and reflection angles are adjusted to be more acute.

The concave mirror 22 is not limited to the spherical mirror. The concave mirror 22 may be, for example, a non-spherical mirror or free-form mirror.

Figure 9A:
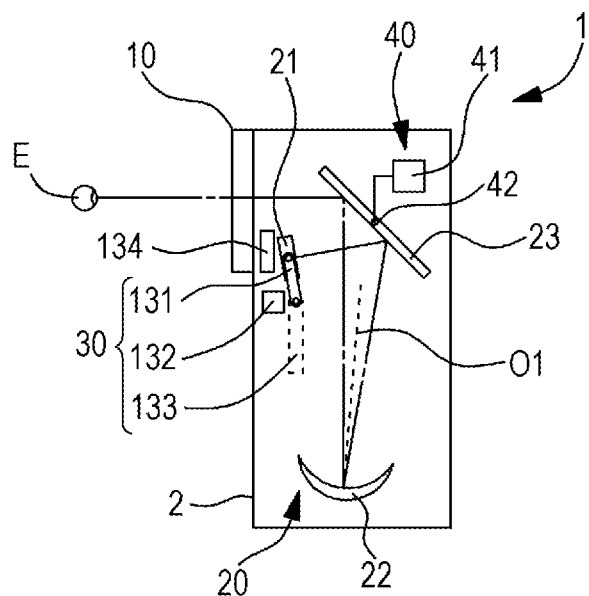
FIGS. 9A and 9B are diagrams illustrating a modification of the apparatus.

The optical arrangement for allowing the target light flux from the display 21 to enter the concave mirror 22 may be, as described above, an arrangement where the target light flux from the display 21 directly enters the concave mirror 22, or an arrangement where the target light flux from the display 21 enters the concave mirror 22 via the optical member 23. For example, as illustrated in FIG. 9A, the target light flux from the display 21 may enter the concave mirror 22 via the optical member 23. In this case, for example, the target light flux emitted from the display 21 is reflected by the optical member 23 and then reflected by the concave mirror 22. The target light flux is subsequently reflected again by the optical member 23 and projected to the examinee's eye E. In other words, in this configuration, the display 21 is configured to emit the target light flux to the optical member 23. Furthermore, the display 21 is configured to be able to take a first attitude where the target light flux emitted from the display 21 is reflected by the optical member 23, travels to the concave mirror 22, is reflected again by the optical member 23 via the concave mirror 22, and is presented to the examinee.

For example, in such an optical arrangement as illustrated in FIG. 9A, a display surface of the display 21 is oriented in the opposite direction to the examinee. In this case, the examinee is prevented from looking directly at the target displayed on the display 21 and therefore an appropriate examination can be performed. Furthermore, there will be no need to place the display 21 away in the up direction to avoid direct projection of the target light flux from the display 21 to the examinee's eye E. Hence, it is allowed to prevent the size of the apparatus 1 in the up-down direction from increasing. Therefore, the examiner can face the examinee across the apparatus 1. Accordingly, the degree of freedom of the installation of the apparatus 1 increases.

Moreover, such an optical arrangement as illustrated in FIG. 9A reduces the possibility that the optical path of the target light flux from the display 21 is blocked by the optical member 23, as compared to the arrangement illustrated in FIG. 2 or 4. Hence, a target light flux without an eclipse by the iris can be projected to the examinee's eye E. Furthermore, there is no need to increase the distance between the display 21 and the optical member 23 to suppress the target light flux eclipsed by the iris. Hence, the width of the apparatus 1 in the front-back direction can be reduced.

Such an optical arrangement as illustrated in FIG. 9A can reduce the distance between the examinee and the target presenting apparatus 1. Hence, the target presenting apparatus 1 and the optometry unit 100 can be integrated. The target presenting apparatus 1 and optometry unit 100 combined in one unit can be operated as a portable optometry system.

Figure 9B:
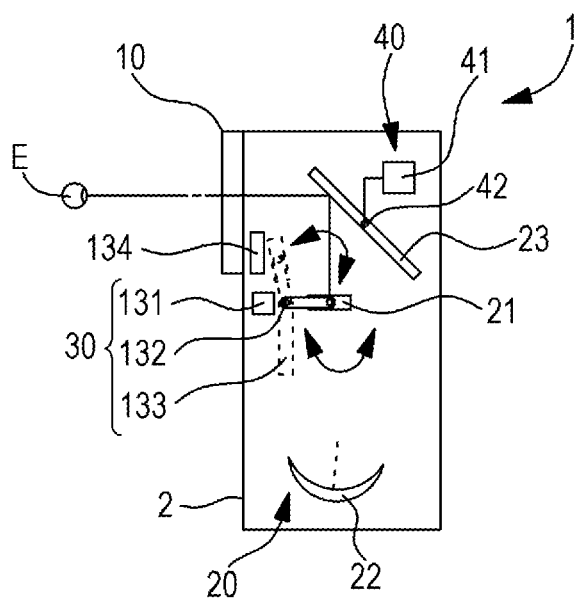

Also such an optical arrangement as illustrated in FIG. 9A may be provided with the above-mentioned near-far switching part 30 to switch the target presentation position (the position of the display 21) in accordance with which of the distance examination and the near examination is performed. For example, the near-far switching part 30 may include a rotary holder 131 that holds the display 21 rotatably. For example, the rotary holder 131 rotates by being driven by a driving part 132. For example, as illustrated in FIG. 9B, the near-far switching part 30 may rotate the rotary holder 131 in such a manner as that the target light flux from the display 21 is reflected by the optical member 23 and presented (projected) to the examinee's eye E not via the concave mirror 22. In this manner, the near-far switching part 30 may be configured to switch the attitude (state) of the display 21 between the first attitude (state) where the target light flux emitted from the display 21 is reflected by the optical member 23, travels to the concave mirror 22, is reflected again by the optical member 23 via the concave mirror 22, and is presented (projected) to the examinee (the examinee's eye E), and a second attitude (state) where the target light flux emitted from the display 21 is reflected by the optical member 23 in such a manner as to travel to the examinee, and presented (projected) to the examinee (the examinee's eye E) not via the concave mirror 22.

The apparatus 1 may include a member for changing the target presentation distance to any presentation distance upon the near examination. For example, the near-far switching part 30 may include a movement part 133. The movement part 133 moves the display 21 in the optical axis direction of the display 21 (the up-down direction in FIG. 9B) upon the near examination. Consequently, the target presentation distance upon the near examination can be changed.

The apparatus 1 may be provided with a shielding part between the examinee's eye E and the display 21 to avoid direct projection of the target light flux from the display 21 to the examinee's eye E upon the near examination. For example, the apparatus 1 may include a shielding part 134 placed between the examinee (the examinee's eye E) and the display 21 as illustrated in FIG. 9B. When the display 21 is moved upon the near examination, the direction of the display surface of the display 21 may change. In this case, for example, the apparatus 1 may shield (block), with the shielding part 134, the target light flux traveling directly to the examinee's eye E from the display 21. Consequently, it is allowed to prevent the examinee from looking directly at the target of the display 21. As a result, an appropriate examination can be performed with the target light flux reflected by the optical member 23. The shielding part 134 may serve as a part of the housing 2. For example, the shielding part 134 may be formed on the housing 2.

Figure 10A:
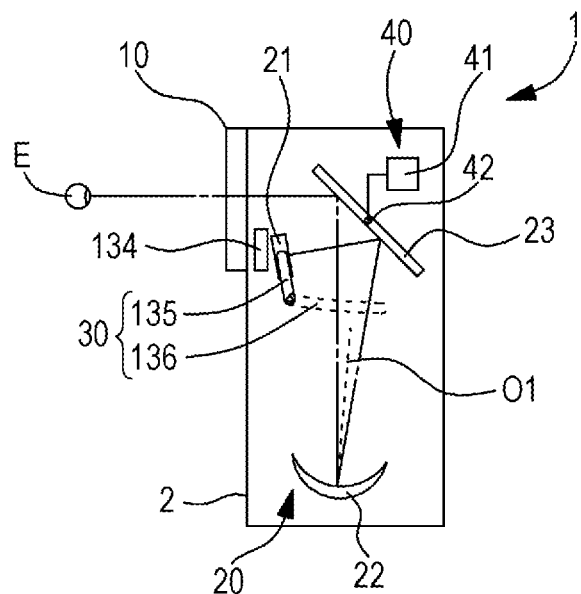
FIGS. 10A and 10B are diagrams illustrating a modification of the apparatus.
Figure 10B:
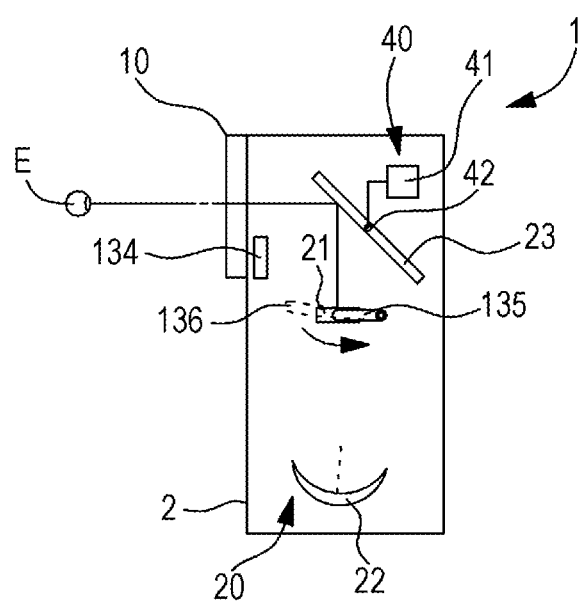

The method for switching the position of the display 21 in accordance with which of the distance examination and the near examination is performed is not limited to the above methods. For example, the near-far switching part 30 may include a slide mechanism. In this case, the display 21 may slide and move from the presentation position for the distance examination to the presentation position for the near examination. For example, as illustrated in FIG. 10A, the near-far switching part 30 may include a holder 135 and a slide part 136. The holder 135 holds, for example, the display 21. The slide part 136 moves, for example, the holder 135 (the display 21) between the presentation position for the distance examination and the presentation position for the near examination. For example, as illustrated in FIG. 10B, the display 21 held by the holder 135, together with the holder 135, is moved by the slide part 136. In this manner, the near-far switching part 30 may switch the position of the display 21 between the presentation position for the distance examination and the presentation position for the near examination by sliding the display 21.

Figure 11:
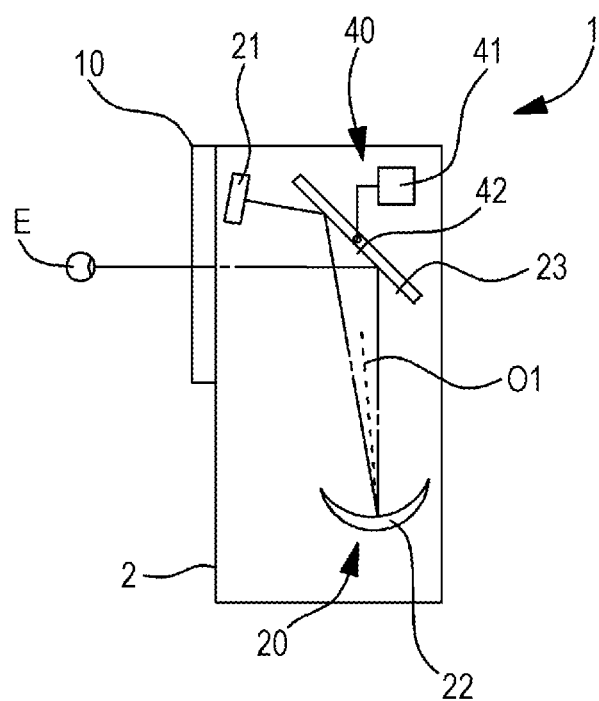
FIG. 11 is a diagram illustrating a modification of the apparatus.

Naturally, the position of the display 21 is not limited to the positions illustrated in FIGS. 9A, 9B, 10A, and 10B. For example, the display 21 may be placed above the visual line of the examinee who observes a target via the protection panel 10 as illustrated in FIG. 11. For example, also in the case illustrated in FIG. 11, the target light flux from the display 21 is reflected by the optical member 23, and then reflected by the concave mirror 22 and again by the optical member 23, and projected to the examinee's eye E.

The embodiment has been described taking the example of the configuration where the display 21, the concave mirror 22, and the optical member 23 are installed in the same housing 2. However, they are not necessarily installed in the same housing 2. For example, at least any of the display 21, the concave mirror 22, and the optical member 23 may be placed in a first housing, and the rest of the members may be placed in a second housing different from the first housing. Alternatively, at least any of the display 21, the concave mirror 22, and the optical member 23 may be placed in the first housing, and the rest of the members may be placed at a position different from the first housing. For example, the display 21 may be provided at a position different from a housing where the concave mirror 22 and the optical member 23 are accommodated.

In the embodiment, the apparatus 1 includes a control system with the control part 70, the controller 90, and the memory 72. Instead, the apparatus 1 may not include the control system. The control system may be included in another apparatus being a separate body from the apparatus 1. In this case, the apparatus including the control system may be connected to the apparatus 1 in a wired or wireless manner.

The near-far switching part 30 can switch the target presentation position between far use and near use by making a replacement between the far-use holder 31 and the near-use holder 32 for the display 21. The far-use holder 31 may hold, for example, the display 21 detachably at a presentation position for a distance visual acuity examination (the presentation position for far use) for the examinee's eye E. The near-use holder 32 may hold, for example, the display 21 detachably at a presentation position for a near visual acuity examination (the presentation position for near use) for the examinee's eye E.

The target presenting apparatus according to the embodiment of the present disclosure may be the following the first to twelfth target presenting apparatuses.

The first target presenting apparatus is a target presenting apparatus for presenting a target to an examinee, and includes a concave mirror that reflects a target light flux, a display for projecting the target light flux, the display being placed in such a manner as that the direction of the normal to a screen of the display is inclined with respect to an optical axis of the concave mirror to allow the target light flux to enter the concave mirror while displacing the target light flux from the optical axis of the concave mirror, a housing for accommodating the concave mirror and the display therein, and an optical member placed in the housing to guide the target light flux emitted by the display and reflected by the concave mirror, from the inside to the outside of the housing, and present the target to the examinee.

In the second target presenting apparatus according to the first target presenting apparatus, the optical member is placed outside an optical path of a first optical path that projects the target light flux from the display to the concave mirror.

In the third target presenting apparatus according to the first target presenting apparatus, the display is placed in an upper part of the housing, and projects the target light flux downward, the concave mirror is placed in a lower part of the housing, and reflects upward the target light flux from the display, and the optical member guides, toward the examinee, the target light flux reflected by the concave mirror and traveling upward.

In the fourth target presenting apparatus according to the first target presenting apparatus, the display is placed closer to the examinee than the optical member.

The fifth target presenting apparatus according to the first target presenting apparatus further includes a driving part that holds the optical member in a drivable manner, the driving part being configured to drive the optical member, and change an optical path upon guiding, to the examinee, the target light flux reflected by the concave mirror.

The sixth target presenting apparatus according to the first target presenting apparatus includes a preventer that is placed above the concave mirror, prevents the concave mirror from becoming dirty, and transmits at least the target light flux when the target light flux is projected from the display.

The seventh target presenting apparatus according to the first target presenting apparatus includes a far-use holder that holds the display detachably at a presentation position for far use with respect to the examinee, and a near-use holder that holds the display detachably at a presentation position for near use with respect to the examinee.

The eighth target presenting apparatus according to the seventh target presenting apparatus includes a back-and-forth movement part that moves the near-use holder in the front-back direction with respect to the examinee.

The ninth target presenting apparatus according to the seventh target presenting apparatus includes an up-and-down movement part that moves the near-use holder in the up-down direction with respect to the examinee.

The tenth target presenting apparatus according to the seventh target presenting apparatus includes an angle adjuster that turns the near-use holder toward the examinee side, the angle adjuster being configured to turn the near-use holder toward the examinee side to change the angle of the screen of the display held by the near-use holder.

In the eleventh target presenting apparatus according to any of the first to tenth target presenting apparatuses, the optical member reflects, toward the concave mirror, the target light flux emitted by the display, guides the target light flux reflected by the concave mirror from the inside to the outside of the housing, and presents the target to the examinee.

The twelfth target presenting apparatus is a target presenting apparatus for presenting a target to an examinee, and includes a concave mirror that reflects a target light flux, a display for projecting the target light flux, the display being placed in such a manner as that the direction of the normal to a screen of the display is inclined with respect to an optical axis of the concave mirror to allow the target light flux to enter the concave mirror while displacing the target light flux from the optical axis of the concave mirror, a housing for accommodating the concave mirror and the display therein, and an optical member placed in the housing to guide the target light flux emitted from the display and reflected by the concave mirror, from the inside to the outside of the housing, and present the target to the examinee.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A target presenting apparatus comprising:
   a display for emitting a target light flux;
   a concave mirror for receiving the target light flux in such a manner as to displace the target light flux from an optical axis thereof;
   a housing for accommodating the concave mirror and the display therein; and
   an optical member, placed in the housing, for guiding the target light flux from the inside to the outside of the housing to present a target to an examinee,
   wherein an optical axis of the target light flux incident to the concave mirror is inclined with respect to the optical axis of the concave mirror;
   the optical member is configured to guide the target light flux reflected by the concave mirror, from the inside to the outside of the housing; and
   the optical member is a total reflection mirror which reflects substantially all of the target light flux incident to the optical member.

2. The target presenting apparatus according to claim 1, wherein
   the display is configured to emit the target light flux to the concave mirror.

3. The target presenting apparatus according to claim 2, wherein
   the display includes a screen for emitting the target light flux, the screen having a normal direction inclined with respect to the optical axis of the concave mirror.

4. The target presenting apparatus according to claim 2, wherein
   the optical member is placed at a position deviating from a first optical path being an optical path of the target light flux travelling from the display to the concave mirror.

5. The target presenting apparatus according to claim 2, wherein
   the display is placed in an upper part of the housing, and emits the target light flux downward,
   the concave mirror is placed in a lower part of the housing, and reflects upward the target light flux from the display, and
   the optical member guides, toward the examinee, the target light flux reflected by the concave mirror and travelling upward.

6. The target presenting apparatus according to claim 2, wherein the display is placed closer to the examinee than the optical member.

7. The target presenting apparatus according to claim 2, further comprising
   a driving unit configured to hold the optical member in a drivable manner, wherein
   the driving unit drives the optical member to change an optical path for guiding, to the examinee, the target light flux reflected by the concave mirror.

8. The target presenting apparatus according to claim 2, further comprising
   a preventer, placed above the concave mirror, configured to prevent the concave mirror from becoming dirty, wherein
   the preventer includes a shielding member for transmitting at least the target light flux emitted from the display.

9. The target presenting apparatus according to claim 2, further comprising:
   a far-use holder configured to hold the display detachably at a presentation position for a distance visual acuity examination; and
   a near-use holder configured to hold the display detachably at a presentation position for a near visual acuity examination, wherein
   when the display is held by the far-use holder, an optical distance between the display and the examinee's eye is longer than the optical distance when the display is held by the near-use holder.

10. The target presenting apparatus according to claim 9, further comprising
    a back-and-forth movement part configured to move the near-use holder in a front-back direction with respect to the examinee.

11. The target presenting apparatus according to claim 9, further comprising
    an up-and-down movement part configured to move the near-use holder in an up-down direction with respect to the examinee.

12. The target presenting apparatus according to claim 9, further comprising
    an angle adjuster configured to turn the near-use holder toward the examinee side, wherein
    the angle adjuster turns the near-use holder toward the examinee side to change an angle of a screen of the display held by the near-use holder.

13. The target presenting apparatus according to claim 1, wherein
    the display is configured to emit the target light flux to the optical member, and
    the display is configured to take a first attitude where the target light flux emitted from the display is reflected by the optical member, travels to the concave mirror, is reflected again by the optical member via the concave mirror, and is presented to the examinee.

14. The target presenting apparatus according to claim 13, further comprising a near-far switching part configured to switch an attitude of the display between the first attitude and a second attitude where the target light flux emitted from the display is reflected by the optical member in such a manner as to travel to the examinee, and is presented to the examinee, wherein when the display is at the first attitude, an optical distance between the display and the examinee's eye is longer than the optical distance at the second attitude.

15. The target presenting apparatus according to claim 13, wherein the display is placed above a visual line of the examinee.

* * * * *